(12) United States Patent
Paillet (10) Patent No.: US 12,427,043 B2
(45) Date of Patent: Sep. 30, 2025

(54) FLEXIBLE MEDICAL APPLIANCE AND METHOD FOR MANUFACTURING SUCH AN APPLIANCE

(71) Applicant: Stéphane Paillet, Visan (FR)

(72) Inventor: Stéphane Paillet, Visan (FR)

( * ) Notice: Subject to any disclaimer, the term of this patent is extended or adjusted under 35 U.S.C. 154(b) by 521 days.

(21) Appl. No.: 17/905,756

(22) PCT Filed: Feb. 26, 2021

(86) PCT No.: PCT/FR2021/050331
§ 371 (c)(1),
(2) Date: Sep. 6, 2022

(87) PCT Pub. No.: WO2021/176165
PCT Pub. Date: Sep. 10, 2021

(65) Prior Publication Data
US 2023/0165694 A1  Jun. 1, 2023

(30) Foreign Application Priority Data
Mar. 6, 2020  (FR) ..................................... 2002261

(51) Int. Cl.
*A61F 2/80* (2006.01)
*A61F 2/50* (2006.01)

(52) U.S. Cl.
CPC .............. *A61F 2/80* (2013.01); *A61F 2/5044* (2013.01); *A61F 2002/5056* (2013.01)

(58) Field of Classification Search
CPC combination set(s) only.
See application file for complete search history.

(56) References Cited

U.S. PATENT DOCUMENTS

| 11,622,870 B1* | 4/2023 | Johnson | A61F 2/64 |
| | | | 623/32 |
| 2008/0188948 A1* | 8/2008 | Flatt | A61F 2/5046 |
| | | | 264/222 |

(Continued)

FOREIGN PATENT DOCUMENTS

| EP | 2856980 B1 | 3/2021 |
| FR | 2539616 A1 | 3/1985 |
| FR | 2828093 B1 | 6/2004 |

OTHER PUBLICATIONS

International Search Report for International Application No. PCT/FR2021/050331 dated Jun. 4, 2021, 2 pages.

(Continued)

*Primary Examiner* — Nitin Patel
(74) *Attorney, Agent, or Firm* — TraskBritt (57) ABSTRACT

A flexible medical appliance intended to be placed on a part of a patient's body and to match its shape comprises a rigid structure having a contour, as well as at least one deformable layer. The appliance further comprises a bonding fabric engaging at least one peripheral portion of the rigid structure extending along its contour, the rest of the bonding fabric forming an exposed portion for receiving the deformable layer. The rigid structure and the deformable layer are assembled edge to edge, the deformable layer completing the rigid structure to form the medical appliance. The present disclosure also proposes a method for manufacturing such an appliance.

19 Claims, 4 Drawing Sheets

(56) References Cited

U.S. PATENT DOCUMENTS

| | | | |
|---|---|---|---|
| 2013/0190895 A1* | 7/2013 | Kristinsdottir | A61F 2/7812 |
| | | | 623/36 |
| 2016/0228266 A1* | 8/2016 | Alley | A61F 2/7812 |
| 2019/0046338 A1 | 2/2019 | Alley et al. | |
| 2020/0383807 A1* | 12/2020 | Volkmar | A61F 2/78 |
| 2021/0137707 A1* | 5/2021 | Hansen | A61F 2/78 |
| 2021/0145613 A1* | 5/2021 | Anderson | A61F 2/5044 |
| 2023/0338168 A1* | 10/2023 | Wagner | B32B 5/26 |
| 2024/0415677 A1* | 12/2024 | Laghi | A61F 2/5046 |

OTHER PUBLICATIONS

International Written Opinion for International Application No. PCT/FR2021/050331 dated Jun. 4, 2021, 5 pages.

\* cited by examiner

FLEXIBLE MEDICAL APPLIANCE AND METHOD FOR MANUFACTURING SUCH AN APPLIANCE

CROSS-REFERENCE TO RELATED APPLICATIONS

This application is a national phase entry under 35 U.S.C. § 371 of International Patent Application PCT/FR2021/050331, filed Feb. 26, 2021, designating the United States of America and published as International Patent Publication WO 2021/176165 A1 on Sep. 10, 2021, which claims the benefit under Article 8 of the Patent Cooperation Treaty to French Patent Application Serial No. FR2002261, filed Mar. 6, 2020.

TECHNICAL FIELD

The present disclosure relates to a flexible medical appliance intended to be arranged on a part of the body of a patient, as well as the method of manufacture thereof. It relates more particularly to the field of prosthetic or orthopedic appliances.

BACKGROUND

A prosthesis is a medical appliance intended to replace a missing limb or part of the limb. It usually consists of a socket to which the synthetic replacement limb is attached. The socket is intended to receive the end of the amputated limb and allows its connection to the synthetic limb. The socket may be custom made to fit the shape and size of the amputated limb.

As European Patent Application EP2856980 recalls, sockets are generally made of resin or of rigid or semi-rigid plastic and comprise an outer structure based on carbon. However, the socket must be comfortable, easy to install, and have a good fit on the amputated limb, particularly so as not to be lost when moving.

To solve this, it is known from the state of the art to use sockets comprising a sleeve, usually made of silicone, placed inside the socket. Silicone is a flexible, deformable, and comfortable material. The sleeve facilitates positioning of the amputated limb in the socket. It also has a comfort function, the sleeve providing contact and cushioning to the amputated limb in the socket, reducing any pain.

However, this type of socket has several drawbacks. It does not take into account volume variations of the stump. The socket may be uncomfortable in a seated position due to its rigidity. Arranging the sleeve on a daily basis each time the prosthesis is used may also be a constraint because of its potential complexity.

A solution to these drawbacks is known from European Patent Application EP2856980 and French Patent Application FR2539616, each of which describes a socket comprising flexible zones and rigid zones, thus forming a flexible socket capable of deforming and of adapting to different stresses. More particularly, the socket of these documents comprises a rigid frame sandwiched by two layers of flexible silicone material. However, this type of socket has the disadvantage of being heavy due to the large amount of flexible material used, silicone being a very dense material.

BRIEF SUMMARY

One object of the present disclosure is to propose a medical appliance that at least partially overcomes this drawback. More particularly, the present disclosure relates to a flexible and light medical appliance, as well as to its method of manufacture. The appliance may be a prosthesis to replace a missing limb of a patient or a part of the limb. It may also be a brace to compensate, temporarily or permanently, for a deficiency or an osteoarticular or muscular deformation of the patient.

With a view to achieving this object, the present disclosure proposes a flexible medical appliance intended to be placed on a part of a patient's body and to match its shape, the flexible medical appliance comprising a rigid structure having a contour, as well as at least one deformable layer.

According to the present disclosure, a bonding fabric is engaged in at least one peripheral portion of the rigid structure extending along its contour, the remainder of the bonding fabric forming an exposed portion to receive the deformable layer. The rigid structure and the deformable layer are assembled edge to edge, the deformable layer completing the rigid structure to form the medical appliance.

The bonding fabric, engaged in the rigid structure and retaining the flexible material of the deformable layer, makes it possible to place the flexible part and the rigid part of the appliance edge to edge. It is therefore not necessary to hold the rigid structure sandwiched together by two layers of flexible material, which reduces the amount of flexible material and the weight of the assembly.

According to other advantageous and non-limiting features of the present disclosure, taken alone or in any technically feasible combination:
  the material of the rigid structure is a carbon-based composite material;
  the material of the bonding fabric is fiberglass;
  the material of the deformable layer is an elastomeric material such as a silicone;
  the deformable layer and the rigid structure do not overlap;
  the medical appliance comprises an inner coating film of deformable material, the inner coating film at least partially covering the inner surface of the rigid structure and the deformable layer;
  the medical appliance comprises an outer coating film made of deformable material, the outer coating film at least partially covering the outer surface of the rigid structure and the deformable layer; and/or
  the rigid structure comprises at least two posts extending substantially axially from a base toward one end.

According to another aspect, the present disclosure proposes a method for manufacturing a flexible medical appliance intended to be placed on a part of a patient's body and to match the shape thereof, the method comprising the following steps:
  providing a positive mold of the part of the body intended to receive the medical appliance;
  forming a rigid structure, provided with an insert on only one portion of the positive mold to preserve a portion of the positive mold called the free portion; and
  forming a deformable layer on the free portion of the positive mold, the formation of the deformable layer comprising the following steps:
    engaging a portion of a bonding fabric in the insert of the rigid structure, the rest of the bonding fabric forming an exposed portion at least partially covering the free portion of the positive mold;
    forming the deformable layer on the exposed portion of the bonding fabric and edge to edge with the rigid structure; and applying a heat treatment to harden the deformable layer.

According to other advantageous and non-limiting features of the present disclosure, taken alone or in any technically feasible combination:

the formation of the rigid structure comprises the following steps:
  forming a first layer of a material able to be stiffened, the first layer having a contour;
  arranging a separation film on at least a part of the first layer to cover at least one peripheral zone extending along the contour of the first layer;
  forming a second layer of a material capable of being stiffened overlapping the first layer, so that the separation film is placed between the first and the second layer at least at the peripheral zone;
  applying a heat treatment to the assembly formed by the first layer, the separation film, and the second layer to obtain the rigid structure, the separation film preventing the sealing of the first layer to the second layer at least in the peripheral zone to define an insert in the rigid structure; and
  extracting the separation film from the rigid structure;
the formation of the first layer and of the second layer comprises the arrangement of a plurality of intermediate layers of material capable of being stiffened;
the formation of the rigid structure comprises a finishing step, the finishing step comprising:
  withdrawing the positive mold;
  trimming the rigid structure to shape the contour of the second layer to that of the first layer;
  sanding the edges of the rigid structure so that the edges have a surface compatible with edge-to-edge bonding; and
  putting the positive mold back in place;
the method for manufacturing a medical appliance comprises a preliminary step, before forming the rigid structure, of forming an inner coating film of deformable material, this preliminary step comprising:
  arranging the inner coating film over the entire surface of the positive mold; and
  a heat treatment to harden the inner coating film;
the preliminary step comprises, following its heat treatment, the arrangement of an isolating film on the inner coating film to isolate it from the rest of the medical appliance during the formation of the rigid structure, the isolating film being removed after the formation of the rigid structure;
the method for manufacturing a medical appliance comprises an additional step of arranging an outer coating film of deformable material to cover the outer surface of the rigid structure as well as that of the deformable layer; and/or
the additional step of forming an outer coating film is carried out between the arrangement of the deformable layer and the heat treatment of the step of forming the deformable layer, the heat treatment of the step of forming the deformable layer simultaneously curing the deformable layer and the outer coating film.

BRIEF DESCRIPTION OF THE DRAWINGS

Other features and advantages of the present disclosure will become apparent from the following detailed description of embodiments of the present disclosure, which is provided with reference to the accompanying figures, in which.

DETAILED DESCRIPTION

Overview of the Socket

Figure 1:
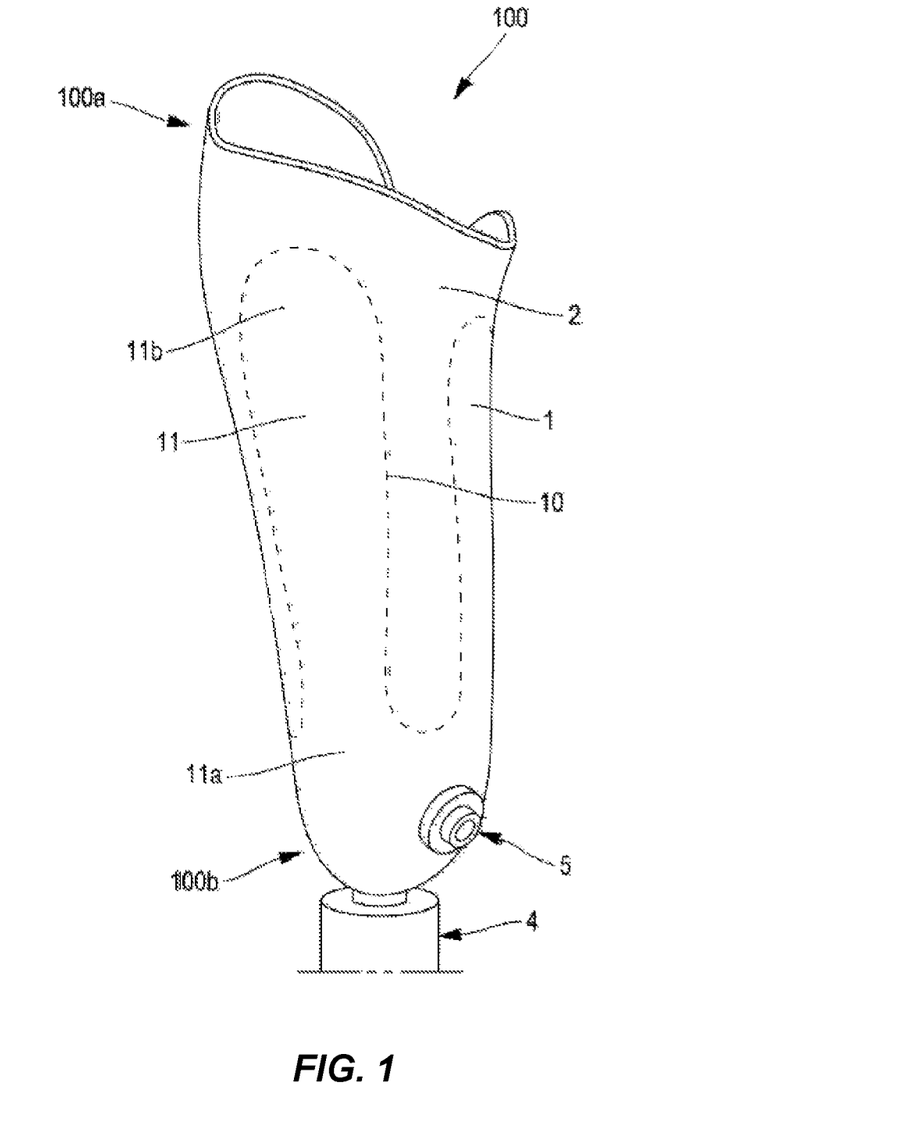
FIG. 1 is an overview of a medical appliance according to the present disclosure.

FIG. 1 is an overview of a medical appliance 100, here a prosthesis socket, according to the present disclosure.

In the remainder of the description, the terms "medical appliance 100," "appliance 100," or "socket 100" will be used interchangeably to designate this appliance.

A medical appliance 100 according to the present disclosure comprises a rigid part and a deformable part. This hybridization makes it possible to provide a socket 100 that is rigid enough to ensure its hold onto the stump while having sufficient flexibility to adapt to various situations, such as variations in volume of the stump. The presence of flexible parts in the socket 100 therefore allows the latter to deform to adapt to this variation in volume, which improves the user's comfort and helps to prevent injuries.

The socket 100 is generally associated with a modular element 4 forming a synthetic member, as well as with a valve 5 for expelling air from the interior of the socket 100 during the introduction of the stump and to form a vacuum, ensuring the fit of the socket to the stump. However, this valve 5 does not form an essential element of the socket 100, and it may be replaced by any other means for keeping the stump and/or a sleeve in the socket, for example a distal hooking means. The socket 100 comprises a proximal part 100a allowing the insertion of the amputated limb as well as a distal part 100b. The modular element 4, as well as the valve 5, are advantageously located on the distal part 100b of the socket 100.

The rigid part of the socket is formed of a rigid structure 1. This rigid structure 1 has a contour 10 and forms the frame of the socket 100. It is formed of a layer of material that may have a thickness typically between 0.5 mm and several millimeters, such as 2 or 3 mm, or even 5 mm. Advantageously, the rigid structure 1 incorporates the distal part 100b of the socket 100 to ensure the solidity of the junction between the socket 100 and the modular element 4. Typically, the rigid structure 1 is made of a composite material comprising carbon, for example, a polymer resin reinforced with carbon fibers. In general, the rigid structure 1 is made of a technical fiber (based on linen, basalt, aramid such as Kevlar, glass, or carbon) and a polymer resin or a plastic material that reinforces this fiber. The resin or the plastic material may be thermosetting or thermoformable.

The rigid structure 1 may have a wide variety of shapes and contours 10. To properly hold the patient's limb, it may advantageously comprise a plurality of posts 11, four posts in the example shown in the figures, extending substantially axially from a base 11a of the distal part 100b toward an end 11b on the side of the proximal part 100a of the socket 100. The ends 11b of the different posts 11 may either be connected together or not, depending on the needs and the desired rigidity. When some of these ends 11b are interconnected, they define openings in the rigid structure 1 delimiting locations for flexible zones. Obviously, the shape shown in the figures is in no way restrictive, and the rigid structure 1 may be given any shape that is suitable according to the nature of the medical appliance and the needs of the patient.

The flexible part of the socket 100 is formed of a deformable layer 2, typically made of an elastomeric material, such as a gel or a silicone rubber. The elastomeric material is preferably a silicone elastomer that is curable at room temperature, called "RTV silicone" (Room Temperature Vulcanization), which is formed by mixing two components, in the presence of a catalyst, which ideally cure at a temperature of between 20° C. and 25° C. The elastomeric material may also be a heat-curable silicone elastomer, called "HTV silicone" (High Temperature Vulcanization). The elastomeric material may also be a thermoplastic elastomer, a polyurethane, or a polyurethane containing fluorine, a copolymer.

The deformable layer 2 has a thickness substantially equivalent to that of the rigid structure 1, typically between 2 mm and 5 mm, in particular, at the junction with the rigid structure 1.

The deformable layer 2 completes the rigid structure 1 to form the medical appliance 100. The deformable layer 2 may be formed in one piece or comprise several separate parts, in particular, when this layer fills openings formed in the rigid structure 1. The deformable layer 2 and the rigid structure 1 are assembled edge to edge, without necessarily overlapping, which constitutes an important feature of the appliance 100. "Edge to edge" means that the rigid structure 1 and the deformable layer 2 are contiguous and are in contact with each other via their edges.

The material constituting the deformable layer 2 generally having no adhesive properties with the material forming the rigid structure 1, and the extent of the surfaces in contact being very small, the present disclosure proposes to use a bonding fabric 3 to allow a robust, edge-to-edge assembly of the deformable layer 2 and the rigid structure 1.

The socket 100 thus comprises a bonding fabric 3 (FIG. 4), a portion of which is engaged at least in a peripheral portion of the rigid structure 1, this peripheral portion extending along its contour 10. The rest of the bonding fabric 3, i.e., the portion of the fabric that is not engaged in the rigid structure, forms an exposed portion 3'. The exposed portion 3' of the bonding fabric 3 is intended to receive the deformable layer 2, the bonding fabric thus allowing the junction between the rigid structure 1 and the deformable layer 2 in order to keep them assembled together.

The bonding fabric 3 comprises a flexible and resistant material, in particular, resistant to shearing, in order to reduce the risk of tearing at the junction between the rigid structure 1 and the deformable layer 2. It may be any technical textile, such as fiberglass, aramid, or plastics, such as high molecular weight polyethylene.

This edge-to-edge assembly configuration makes it possible to reduce the quantity of flexible material forming the deformable layer 2 necessary to form the socket 100 and thus reduce its weight, the deformable layer 2 not necessarily covering the rigid structure 1. It is not necessary, as is the case in the state of the art, to sandwich the rigid part in the flexible part to keep it assembled thereto, the inner surface and the outer surface of the rigid part each being covered by at least one deformable layer.

According to a first variant of the present disclosure, the socket 100 may advantageously comprise an inner coating film of deformable material that may be made of the same kind as that of the deformable layer 2, for example, silicone. The inner coating film covers the inner surface of the rigid structure 1, as well as that of the deformable layer 2. The inner coating film makes it possible to improve the user's comfort while maintaining a socket 100 that is lighter than those of the state of the art. The coating film may have a reduced thickness, less than 2 mm, because it provides a comfort and/or sealing function, and in no way ensures the cohesion of the rigid structure 1 and of the deformable layer 2.

According to a second variant of the present disclosure, the socket 100 may comprise an outer coating film made of a deformable material, the film possibly being of the same kind as that of the deformable layer 2. The outer coating film covers the outer surface of the rigid structure 1, as well as that of the deformable layer 2. The outer coating film makes it possible to improve the aesthetics of the socket 100 while maintaining a socket 100 that is lighter than in the state of the art. Just like the inner coating film, the outer coating film may have a reduced thickness, less than 2 mm.

It is of course possible to envisage combining these two variants and proposing a socket comprising both an inner and an outer coating film. Since these films are not very thick, the weight gain compared to the solutions of the state of the art is maintained.

Method for Manufacturing the Medical Appliance

The method for manufacturing the appliance is based on a very conventional manufacturing method.

Figure 2:
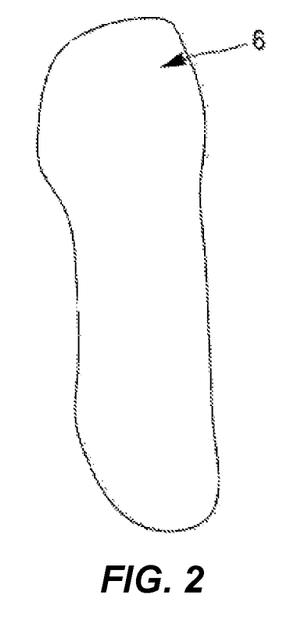
FIG. 2 shows a positive mold of the part of a patient's body intended to receive a medical appliance according to the present disclosure.

Thus, a first step of the method for manufacturing the prosthesis taken as an example comprises providing, by any means known per se, a positive mold 6 of the part of the body of a patient intended to receive the socket 100 (FIG. 2). It may be a positive mold made of plaster, obtained by molding the part of the body in question.

Figure 3A:
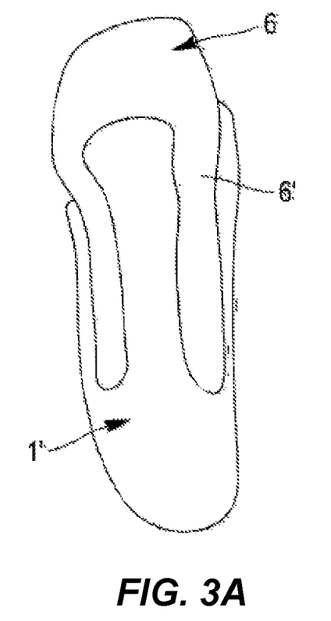
FIGS. 3A to 3D illustrate different stages in the formation of a rigid structure.
Figure 3B:
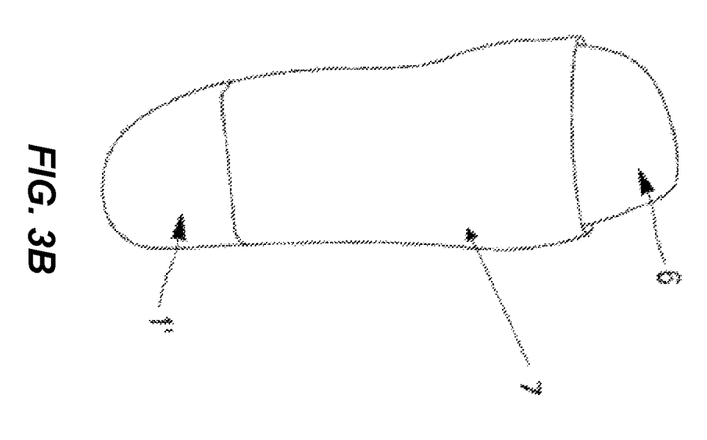

The second step of the method comprises the formation of the rigid structure 1, the structure being provided with an insert 12 (FIG. 3D) to receive the bonding fabric 3. The rigid structure 1 is formed only on a portion of the positive mold 6 to give this structure a desired shape, here a shape comprising a plurality of posts 11. A portion of the positive mold 6, designated the free portion 6' (FIG. 3A), thus remains free of any rigid structure 1. A part of this free portion 6' will subsequently accommodate the deformable layer 2.

This second step of forming the rigid structure 1 comprises several sub-steps, represented in FIGS. 3A to 3D, which will now be described in detail. In a first sub-step (FIG. 3A), a first layer 1' of a material capable of being stiffened is formed on the chosen portion of the positive mold 6. It may thus involve arranging strips or sheets of fiber, for example, made of carbon, impregnated with thermosetting polymer resin on the positive mold. Alternatively, it may also be sheets or strips of a technical fiber (such as those previously mentioned herein) that are impregnated, after having affixed them to the positive mold, with a thermosetting or thermoformable polymer resin. The first layer 1' has a contour 10 substantially conforming to the chosen shape of the rigid structure 1. The formation of the first layer 1' may comprise the arrangement of a plurality of intermediate layers, for example, in the form of sheets or strips. The first layer 1' may thus comprise a stack of three to ten intermediate layers, for example, five intermediate layers, for example, made of carbon fiber pre-impregnated with resin.

In a second sub-step (FIG. 3B) a separation film 7, for example, made of Teflon, is arranged on at least part of the first layer 1'. The purpose of the separation film 7 is to delimit the dimensions of the insert 12, which it aims to form in the rigid structure 1 and which will make it possible to accommodate the bonding fabric. In the example shown, the separation film covers the entire surface of the posts 11 without entirely covering the base 11*a*. More generally, the separation film 7 may advantageously, in order to facilitate its handling, protrude from the first layer 1' and cover the free portion 6' of the positive mold 6. It is also possible for the separation film 7 to entirely cover the first layer 1' or for it to cover only a peripheral zone of this first layer 1' extending along its contour 10', depending on the geometric features desired for the insert 12.

In a third sub-step (FIG. 3C), a second layer 1" made of a material capable of being stiffened is formed, in the same way the first layer 1' was formed, covering the first layer 1', so that the separation film 7 is placed between the first and the second layer 1', 1". In other words, the separation film 7 is sandwiched between the first and the second layer 1', 1", here in the region intended to form the posts 11. The second layer 1" may also be formed from carbon fiber impregnated with thermosetting resin. The second layer 1" may be formed of a stack of three to ten intermediate layers, for example, five intermediate layers of carbon fiber impregnated with resin.

Figure 3C:
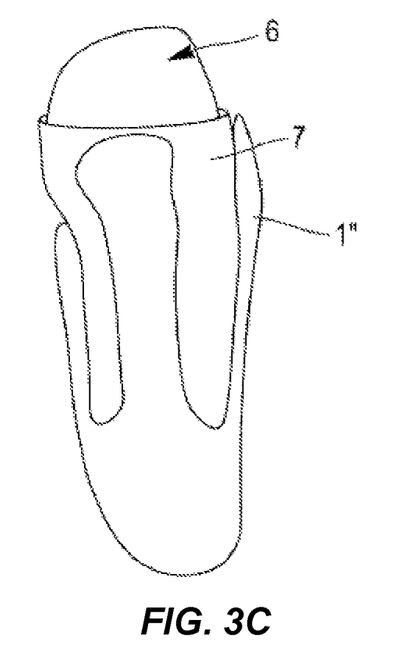
Figure 3D:
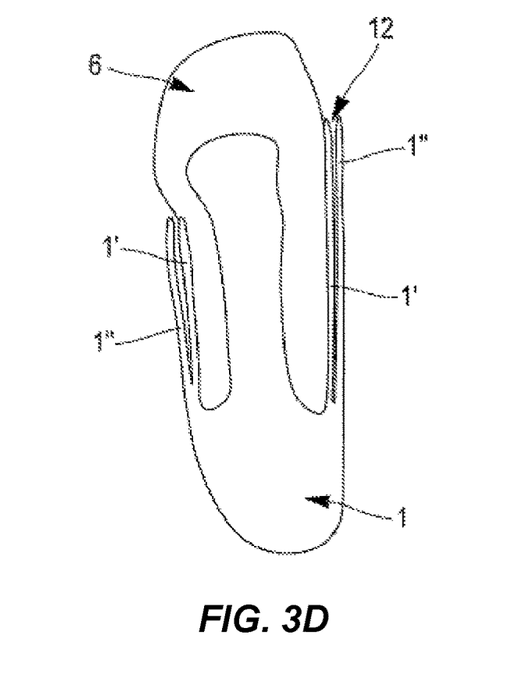

In a fourth, optional sub-step, a heat treatment is applied to the assembly formed of the first layer 1', the separation film 7, and the second layer 1" to accelerate the curing of the resin and to obtain the rigid structure 1. Advantageously, the heat treatment is preceded by placing this assembly under vacuum. Placing it under vacuum makes it possible to achieve good impregnation of the fibers by the resin making up the material of the first and second layers 1', 1" and makes it possible to remove the excess resin in order to create a composite material free of imperfections. The heat treatment accelerates the polymerization/thermal curing of the resin. This may comprise bringing the assembly to a temperature of approximately 100° C. for a period of at least one hour.

The presence of the separation film 7 makes it possible to prevent the sealing of the first layer 1' to the second layer 1" on the portion occupied by this film 7. In this way, the insert 12 is defined, making it possible to receive the bonding fabric 3. Thus, in the example shown, the first layer 1' and the second layer 1" are only sealed together at their base 11*a*, but not at the posts 11. It should be noted that it is possible for the first layer 1' and the second layer 1" to be entirely separated from each other in the case in which the separation film 7 entirely covers the first layer 1'. In such a configuration, the rigid structure 1 comprises two parts fitting perfectly into one another.

In a fifth sub-step (FIG. 3D), the separation film 7 is extracted from the rigid structure 1. In this way, an insert 12 is defined in the rigid structure 1, the insert being able to be used, as will be explained later, to place a portion of a bonding fabric 3 therein.

The step of forming the rigid structure 1 may also include an additional sub-step of finishing the rigid structure 1. In this case, the rigid structure 1 of the positive mold 6 is removed, and the positive mold is mechanically trimmed to give it the desired shape. The edges of the rigid structure 1 may be sanded and its outer and/or inner surfaces may also be smoothed or treated to improve its comfort and/or its shape and promote its adhesion to the outer and inner coating films when they are provided. The finished rigid structure 1 is then again placed on the positive mold 6.

During the formation of the rigid structure 1, if necessary, the modular element 4 and the valve 5 may be assembled on the rigid structure 1 according to techniques known to those skilled in the art.

Continuing the general description of the method for manufacturing the medical appliance 100, the medical appliance comprises a third step of forming the deformable layer 2. This step comprises several sub-steps that will now be described in detail.

Figure 4:
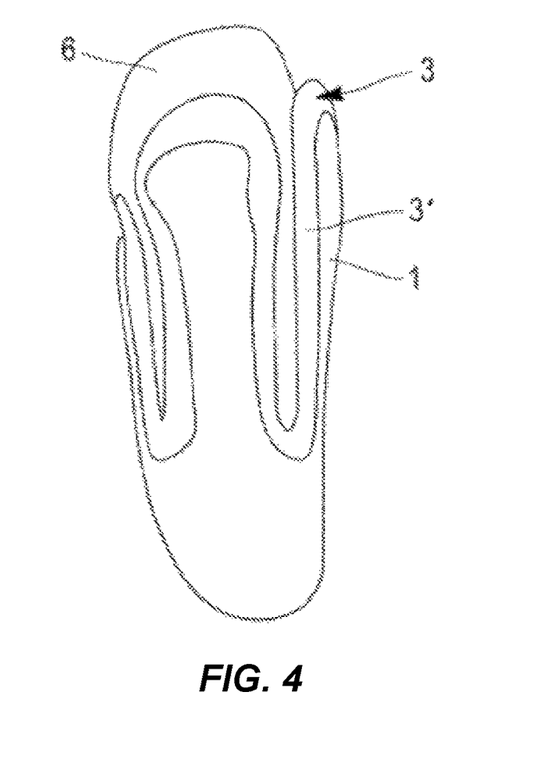
FIG. 4 shows a step of forming a deformable layer.

In a first sub-step of this third step, a portion of the bonding fabric 3, for example, made of fiberglass as already mentioned, is engaged in the insert 12 of the rigid structure 1 (FIG. 4). To facilitate this insertion, the two rigid parts defining the insert 12 may be separated from each other. The remaining part of the bonding fabric 3, i.e., the part not engaged in the insert 12, forms an exposed portion 3', which covers at least part of the free portion 6' of the positive mold 6. Advantageously, the bonding fabric 3 is first coated with glue on the portion intended to engage the insert 12 in order to secure it to the rigid structure.

In a second sub-step, the material intended to form the deformable layer 2, for example, a rubber or a silicone gel as already mentioned, is arranged on the positive mold 6. More precisely, the material intended to form the deformable layer 2 is arranged directly on the exposed portion 3' of the bonding fabric 3 and, if necessary, directly on the free portion 6' of the positive mold 6. The deformable layer 2 at least partially covers the exposed portion 3' of the bonding fabric 3 to fill the space complementary to the rigid structure with flexible material. The rigid structure 1 and the deformable layer 2 are then contiguous, edge to edge. The deformable layer 2 completes the rigid structure 1 to form the medical appliance 100.

In an alternative embodiment, the two sub-steps that have just been described may be inverted. In this case, the deformable layer 2 is placed directly on at least part of the free portion 6' of the positive mold 6, adjoining the rigid structure, before inserting the bonding fabric 3 into the insert 12. It is ensured that the material forming the rigid layer impregnates well the bonding fabric 3.

In any case, the deformable layer 2 completes the rigid structure 1 to form the medical appliance 100, the rigid structure 1 and the deformable layer 2 being arranged contiguously one against the other, edge to edge.

It is possible to envisage treating the outer surface of the deformable layer 2, for example, making it smooth and/or giving it a particular appearance.

In a third sub-step of the third step of forming the deformable layer 2, a heat treatment is applied to harden the deformable layer 2. Advantageously, the heat treatment is preceded by placement under vacuum, which makes it possible to properly impregnate the bonding fabric 3 with the material of the deformable layer, to ensure good contact between this layer 2 and the positive mold 6, as well as with the edge of the rigid structure 1. The heat treatment may be heated in an oven, which makes it possible to harden the deformable layer 2. It may comprise, depending on the nature of the material forming the deformable layer 2, placing the deformable layer at a temperature of approximately 100° C. for several minutes to several hours.

At the end of this sub-step, the deformable layer 2 is kept assembled edge to edge with the rigid structure 1 by way of the bonding fabric 3.

Thus, a complete flexible appliance 100 is obtained, the deformable layer 2 being juxtaposed to the rigid structure 1 just enough to complete this structure, without excess material that could weigh down the appliance.

It is of course possible to provide other manufacturing steps in addition to those that have just been described. Thus, and according to a first variant, the manufacturing method may comprise a preliminary step, before the formation of the rigid structure 1, of forming an inner coating film. To this end, a film of a deformable material, for example, a silicone gum, is produced on the positive mold 6. Then, a heat treatment is applied, preferably heating in an oven preceded by placement under vacuum, to harden the inner coating film. An isolating film, for example, of polyvinyl chloride (PVC) or polyvinyl alcohol (PVA), is then formed on the inner coating film to isolate it during the formation of the rigid structure 1 and prevent their adhesion. The presence of the isolating film makes it possible to easily separate the rigid structure 1 from the inner coating film to allow the application of the finishing step to this structure. The isolating film is removed when the finishing of the rigid structure 1 is completed, in order to place the rigid structure into contact with the inner coating film when this rigid structure 1 is put back on the positive mold 6. Provision may be made to bond the rigid structure 1 and the inner coating film to one another.

According to another variant, the manufacturing method comprises a step of forming an outer coating film, after or during the third step of forming the deformable layer 2. This step comprises the formation of a film made of a deformable material, for example, silicone gum, on the outer surface of the rigid structure 1. This step is advantageously carried out during or after the formation of the deformable layer 2 and before its heat treatment, the heat treatment resulting in the simultaneous hardening of the deformable layer 2 and the outer coating film.

Obviously, the present disclosure is not limited to the embodiment described, and it is possible to add variants without departing from the scope of the present disclosure as defined by the claims.

The present disclosure is, in particular, in no way limited to the prosthesis given as an example, and it is possible to envisage designing on the same principles any form of medical appliance, prosthesis, or brace, for example, a corset or a hand brace.

It is of course possible to give any shape to the rigid structure, depending on the needs of the patient and the nature of the medical appliance, and the present disclosure is in no way limited to the rigid structure shown in the figures.

It is also possible to envisage integrating into the appliance elements other than the modular element 4 and the valve 5, for example, an element allowing the identification of the appliance, such as an RFID tag.

Other ways of manufacturing this appliance may of course be envisaged. In particular, a method could be envisaged in which the various components of the appliance are successively stacked on the positive mold and then exposed to a heat treatment. For example, after arranging the first layer of a material capable of being stiffened on the positive mold, the free portion of the positive mold is directly covered by part of the material intended to form the deformable layer. Then the bonding fabric is arranged on the first layer so as to have an "exposed" portion in contact with the material intended to form the deformable layer. Then the second layer of a material capable of being stiffened is arranged on the first layer to sandwich the bonding fabric. Finally, the rest of the material intended to form the deformable layer is arranged on the part previously arranged, and at least partially covered by the bonding fabric, to form the deformable layer, then a heat treatment is applied to the assembly to finish the appliance.

The invention claimed is:

1. A medical appliance configured to be placed on a part of a body of a patient and to match a shape of the part of the body, the medical appliance comprising:
 a rigid structure having a contour;
 at least one deformable layer;
 a bonding fabric engaged in at least one peripheral portion of the rigid structure extending along the contour of the rigid structure, a remainder of the bonding fabric forming an exposed portion receiving the deformable layer; and
 an inner coating film of deformable material, the inner coating film at least partially covering an inner surface of the rigid structure and the deformable layer;
 wherein the rigid structure and the deformable layer are assembled edge to edge, the deformable layer completing the rigid structure to form the medical appliance.

2. The medical appliance of claim 1, wherein the rigid structure comprises a carbon-based composite material.

3. The medical appliance of claim 2, wherein the bonding fabric comprises fiberglass.

4. The medical appliance of claim 3, wherein the deformable layer comprises an elastomeric material.

5. The medical appliance of claim 4, further comprising an inner coating film of deformable material, the inner coating film at least partially covering an inner surface of the rigid structure and the deformable layer.

6. The medical appliance of claim 5, further comprising an outer coating film of deformable material, the outer coating film at least partially covering an outer surface of the rigid structure and the deformable layer.

7. The medical appliance of claim 1, wherein the bonding fabric comprises fiberglass.

8. The medical appliance of claim 1, wherein the deformable layer is comprises an elastomeric material.

9. The medical appliance of claim 8, wherein the elastomeric material comprises silicone.

10. The medical appliance of claim 1, further comprising an outer coating film of deformable material, the outer coating film at least partially covering an outer surface of the rigid structure and the deformable layer.

11. The medical appliance of claim 1, wherein the rigid structure comprises at least two posts extending substantially axially from a base toward an end.

12. A method for manufacturing a medical appliance configured to be placed on a part of a body of a patient and to match a shape of the part of the body, the method comprising the following steps:
 providing a positive mold of the part of the body;
 forming a rigid structure provided with an insert on only a portion of the positive mold and preserving a free portion of the positive mold;
 forming a deformable layer on the free portion of the positive mold, the forming of the deformable layer comprising the following steps:
  engaging a portion of a bonding fabric in the insert of the rigid structure, a remainder of the bonding fabric forming an exposed portion at least partially covering the free portion of the positive mold;
  forming the deformable layer on the exposed portion of the bonding fabric and edge to edge with the rigid structure; and
  applying a heat treatment to harden the deformable layer.

13. The method of claim 12, wherein the forming of the rigid structure comprises the following steps:
 forming a first layer comprising a material capable of being stiffened, the first layer having a contour;
 arranging a separation film on at least part of the first layer to cover at least one peripheral zone extending along the contour of the first layer;

forming a second layer comprising a material capable of being stiffened overlapping the first layer, so that the separation film is between the first layer and the second layer at least at the peripheral zone;

applying a heat treatment to an assembly formed by the first layer, the separation film, and the second layer to obtain the rigid structure, the separation film preventing the sealing of the first layer to the second layer at least in the peripheral zone to define an insert in the rigid structure; and extracting the separation film from the rigid structure.

14. The method of claim 13, wherein the forming of the first layer and the forming of the second layer comprises arranging a plurality of intermediate layers of material capable of being stiffened.

15. The method of claim 13, wherein the forming of the rigid structure comprises a finishing step, the finishing step comprising:

removing the positive mold;

trimming the rigid structure to shape the contour of the second layer to that of the first layer;

sanding the edges of the rigid structure so that the edges have a surface compatible with edge-to-edge bonding; and putting the positive mold back in place.

16. The method of claim 12, further comprising a preliminary step, before the of the rigid structure, of forming an inner coating film of deformable material, the preliminary step comprising:

arranging the inner coating film over the entire surface of the positive mold; and a heat treatment to harden the inner coating film.

17. The method of claim 16, wherein the preliminary step comprises, following the heat treatment, arranging an isolating film on the inner coating film to isolate it from the rest of the medical appliance during the forming of the rigid structure, and removing the isolating film after the forming of the rigid structure.

18. The method of claim 12, further comprising an additional step of arranging an outer coating film of deformable material to cover the outer surface of the rigid structure and the outer surface of the deformable layer.

19. The method of claim 18, wherein the additional step of forming the outer coating film is carried out between the arranging of the deformable layer and the heat treatment of the step of forming the deformable layer, the heat treatment of the step of forming the deformable layer simultaneously curing the deformable layer and the outer coating film.

* * * * *